United States Patent [19]

Böhm et al.

[11] Patent Number: 5,420,309
[45] Date of Patent: May 30, 1995

[54] FLUORINATED 1,3-BENZO- AND 1,3-PYRIDO-DIOXOLES, THEIR PREPARATION AND THEIR USE

[75] Inventors: Stefan Böhm, Köln; Albrecht Marhold, Leverkusen, both of Germany

[73] Assignee: Bayer Aktiengesellschaft, Leverkusen, Germany

[21] Appl. No.: 145,431

[22] Filed: Oct. 29, 1993

[30] Foreign Application Priority Data

Nov. 6, 1992 [DE] Germany .......................... 42 37 579.7

[51] Int. Cl.[6] .......................................... C07D 317/46
[52] U.S. Cl. ..................... 549/439; 549/437; 549/436; 549/333
[58] Field of Search ............... 549/444, 443, 440, 437, 549/436, 434, 433, 439

[56] References Cited

U.S. PATENT DOCUMENTS

| 3,948,952 | 4/1976 | Gates et al. |
| 4,155,915 | 5/1979 | Arndt et al. |
| 4,838,924 | 6/1989 | Takematsu et al. |

FOREIGN PATENT DOCUMENTS

| 011179 | 5/1980 | European Pat. Off. |
| 042533 | 12/1981 | European Pat. Off. |
| 596361 | 5/1994 | European Pat. Off. |
| 2624822 | 12/1977 | Germany |
| 9411349 | 5/1994 | WIPO |
| 9411350 | 5/1994 | WIPO |
| 9411352 | 5/1994 | WIPO |
| 9411351 | 6/1994 | WIPO |

OTHER PUBLICATIONS

R. Berthold et al., Halvetica Chimica Acta, 55, No. 7, 2461–2467 (1972).
A. Henne et al., Jour. Indian Chem. Soc., 80, No. 12, pp. 809–811 (1953).
J. Chem. Soc. Perkin Trans. I 1987, 763–767, "Polyhalogenoheterocyclic Compounds. Part 38. Reactions of Fluorinated-Alkanes and -Cycloalkanes . . . ".

*Primary Examiner*—Nicky Chan
*Attorney, Agent, or Firm*—Sprung Horn Kramer & Woods

[57] ABSTRACT

Novel fluorinated 1,3-benzo- and 1,3-pyrido-dioxoles of formula (I):

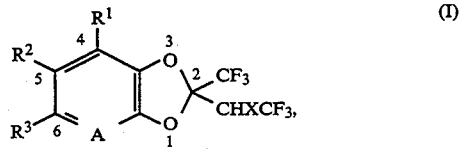

in which
A is C-R$^4$ or N,
X is hydrogen, fluorine, chlorine or bromine and
R$^1$ to R$^4$ can be identical to or different from one another and are each hydrogen, halogen, C$_1$–C$_6$-alkyl, C$_1$–C$_6$-alkoxy, halogeno-C$_1$–C$_6$-alkyl, C$_6$–C$_{10}$-aryl, CHO, COOH, COCl, CN, OH, NCO, COO—C$_1$–C$_6$-alkyl, NO$_2$, NH$_2$, NH—C$_1$–C$_6$-alkyl, N(C$_1$–C$_6$-alkyl)$_2$, SO$_2$Cl, SO$_3$H, SO$_3$Na or SO$_3$K, it also being possible for two adjacent radicals from the series R$^1$ to R$^4$ together to be an optionally substituted —CH=CH—CH=CH— bridge, processes for their preparation and their use for the preparation of plant protection agents.

2 Claims, No Drawings

FLUORINATED 1,3-BENZO- AND 1,3-PYRIDO-DIOXOLES, THEIR PREPARATION AND THEIR USE

The present invention relates to novel fluorinated 1,3-benzodioxoles and novel 1,3-pyridodioxoles, to their preparation and to their use as intermediates for the preparation of plant protection agents.

German Offenlegungsschrift 26 24 822 has disclosed 1,3-benzodioxoles in which the carbon atom in the 2-position can be substituted by 1 or 2 halogenated aliphatic hydrocarbon radicals, e.g. chloromethyl. They are used to prepare firstly the corresponding 5-amino-1,3-benzodioxole and from this a urea derivative.

J. Chem. Soc. Perkin Trans. I, 1987, 763, describes the preparation of 1,3-benzodioxoles which contain fluorinated, usually cyclic but always ethylenically unsaturated radicals in the 2-position.

1,3-Benzodioxoles and 1,3-pyridodioxoles containing $CF_3$ groups in the 2-position have not yet been disclosed.

Fluorinated 1,3-benzo- and 1,3-pyrido-dioxoles of formula (I):

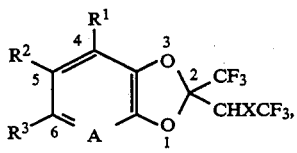

(I)

have now been found in which

A is C—$R^4$ or N,

X is hydrogen, fluorine, chlorine or bromine and $R^1$ to $R^4$ can be identical to or different from one another and are each hydrogen, halogen, $C_1$-$C_6$-alkyl, $C_1$-$C_6$-alkoxy, halogeno-$C_1$-$C_6$-alkyl, $C_6$-$C_{10}$-aryl, CHO, COOH, COCl, CN, OH, NCO, COO—$C_1$-$C_6$-alkyl, $NO_2$, $NH_2$, NH—$C_1$-$C_6$-alkyl, N($C_1$-$C_6$-alkyl)$_2$, $SO_2Cl$, $SO_3H$, $SO_3Na$ or $SO_3K$, it also being possible for two adjacent radicals from the series $R^1$ to $R^4$ together to be an optionally substituted —CH=CH—CH=CH— bridge.

Preferably, in formula (I), A is C—$R^4$ and X is hydrogen or chlorine; and preferably, at least one of $R^2$ and $R^3$ represents an $NH_2$ radical.

If the radicals $R^1$ to $R^4$ are halogen or halogeno-$C_1$-$C_6$-alkyl, halogen is for example fluorine, chlorine or bromine.

Examples of substituents which an optionally substituted —CH=CH—CH=CH— bridge can contain are those indicated above for $R^1$ to $R^4$.

Preferably, at least two of the radicals $R^1$ to $R^4$ are hydrogen and the remaining radical or radicals, provided they are not also hydrogen, independently of one another are preferably chlorine, bromine, methyl, ethyl, $CH_2Cl$, $CH_2Br$, phenyl, CHO, COO, OH, NCO, $NO_2$, $NH_2$ and/or $SO_2Cl$. If two adjacent radicals from the series $R^1$ to $R^4$ are an optionally substituted —CH=CH—CH=CH— bridge, these are preferably the radicals $R^2$ and $R^3$.

A preferred process according to the invention for the preparation of 1,3-benzo- and 1,3-pyrido-dioxoles of formula (I) is characterised in that 1,2-dihydroxybenzenes or 2,3-dihydroxypyridines of formula (II):

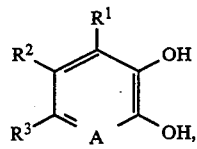

(II)

in which

A and $R^1$ to $R^3$ are as defined for formula (I) except that $R^1$ to $R^3$ are not OH, COCl or $SO_2Cl$, are reacted, in the presence of a base and a diluent, at −20° to +200° C., with a hexafluorobutene of formula (III):

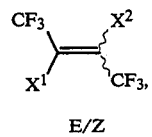

(III)

E/Z in which $X^1$ is hydrogen or halogen and $X^2$ is halogen,

Preferably in formula (III), $X^1$ is hydrogen, fluorine or chlorine and $X^2$ is fluorine or chlorine.

The compounds of formulae (II) and (III) required as starting compounds are known or can be obtained analogously to known compounds. As an example, 0.8 to 1.2 mol of hexafluorobutene of formula (III) can be used per mol of dihydroxy compound of formula (II). This ratio is preferably 1:0.9 to 1.1 and particularly preferably 1:1.

Suitable bases are practically all the common bases, e.g. sodium hydroxide, potassium hydroxide, sodium carbonate, potassium carbonate, DBN (=1,5-diazabicyclo[4.3.0]-non-5-ene), DBU (=1,8-diazabicyclo[4.3.0]-undec-7-ene), pyridine and aliphatic amines. Organic bases are preferably used in anhydrous form; inorganic bases can also be used as aqueous solutions. The bases can be used for example in amounts of 1 to 5 equivalents per mol of compound of formula (II). This amount is preferably 1.5 to 2.5 equivalents.

Suitable diluents are those which do not contain acidic hydrogen atoms, for example aliphatic land aromatic hydrocarbons, halogenated hydrocarbons and ethers. Dipolar aprotic solvents, such as dimethyl sulphoxide, N-methylpyrrolidone, HMPT (=hexamethylphosphoric acid triamide), dimethylformamide and acetonitrile, are preferred. Diluents are preferably used in amounts of 100 to 3000 g per mol of compound of formula (II).

This process according to the invention can be carried out at reduced pressure, normal pressure or elevated pressure. It is preferably carried out at normal pressure or, especially when low-boiling starting materials or auxiliaries and higher reaction temperatures are used, at elevated pressure so that the reaction mixture is present essentially in the liquid phase.

The reaction temperatures are preferably in the range 0° to 150° C. and particularly preferably in the range 20° to 80° C.

This process according to the invention is illustrated by Examples 1 to 11, Example 2 describing a very particularly preferred procedure.

Another process according to the invention for the preparation of 1,3-benzo- and 1,3-pyrido-dioxoles of formula (I) is characterised in that 1,2-dihydroxybenzenes or 2,3-dihydroxypyridines, carrying a protecting group, of formula (IV):

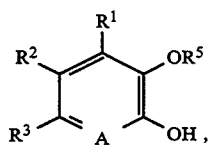

in which

A and $R^1$ to $R^3$ are as defined for formula (I) and
$R^5$ is a protecting group or
$R^5$ and $R^1$ together are a —C(CH$_3$)$_2$—O— radical,
are initially reacted with a hexafluorobutene of formula (III):

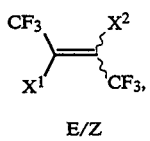

in which
$X^1$ is hydrogen or halogen and
$X^2$ is halogen,
to give an intermediate of formula (V):

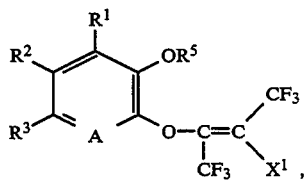

in which
A and $R^1$ to $R^3$ are as defined for formula (I),
$R^5$ is as defined for formula (IV) and
$X^1$ is as defined for formula (III),
the protecting group $R^5$ is cleaved from the intermediate of formula (V) and the resulting OH compound is reacted with a base to give 1,3-benzo- or 1,3-pyrido-dioxoles of formula (I).

In formula (IV), $R^5$ is preferably C$_1$-C$_4$-alkyl, especially methyl, or benzyl, or $R^5$ and $R^1$ together are a —C(CH$_3$)$_2$—O— radical. The compounds of formula (IV) can easily be obtained, for example by introducing a protecting group into compounds of formula (II) in a manner known per se, for example by reaction with dimethyl sulphate, benzyl chloride, 2,2-dimethoxypropane or similar agents.

The reaction of a compound of formula (IV) with a hexafluorobutene of formula (III) can be carried out analogously to the above-described reaction of a compound of formula (II) with a hexafluorobutene of formula (III). However, the preferred reaction temperature here is −10° to +50° C. and the base here is preferably used in amounts of 1.0 to 1.2 equivalents per mol of compound of formula (IV).

The cleavage of the protecting group $R^5$ from the resulting intermediate of formula (V) can be effected for example by carrying out an acidic ether cleavage with hydrogen bromide in the case where $R^5$=C$_1$-C$_4$-alkyl, or a hydrogenolytic cleavage in the case where $R^5$=benzyl.

The resulting OH compound is converted to a 1,3-benzo- or 1,3-pyrido-dioxole of formula (I) by reaction with a base. A possible procedure here is e.g. to react the compound of formula (V) in which $R^5$=hydrogen, optionally in a solvent, with a catalytic amount of a base (analogously to the above-described procedure) at temperatures in the range −10° to +100° C.

The base is preferably added in an amount of 0.01 to 1 equivalent per mol of OH compound.

The process for the preparation of 1,3-benzo- and 1,3-pyrido-dioxoles from 1,2-dihydroxybenzenes and 2,3-dihydroxypyridines, carrying protecting groups, of formula (IV) is illustrated by Examples 12 to 23.

1,3-Benzo- and 1,3-pyrido-dioxoles of formula (I) which are unobtainable or obtainable only with difficulty by the processes described hitherto are accessible by initially preparing unsubstituted or differently substituted 1,3-benzo- or 1,3-pyrido-dioxoles and modifying them.

Examples of such modifications of compounds of formula (I) are the introduction of nitro or halogen groups as substituents $R^1$ to $R^4$, preferably as substituents $R^2$ and/or $R^3$, by electrophilic aromatic substitution, the exchange of halogen groups with cyano groups, the halogenation of alkyl side-chains to halogenoalkyl side-chains and the hydrogenation of NO$_2$ substituents to NH$_2$ substituents. Such modifications are known per se (see e.g. Houben-Weyl, Methoden der organischen Chemie (Methods of Organic Chemistry), volume E5, volume V (4), volume XI (1) etc.).

One particular modification is the hydrogenation of 1,3-benzo-and 1,3-pyrido-dioxoles of formula (I) in which X=chlorine to give 1,3-benzo- and 1,3-pyrido-dioxoles in which X=hydrogen. Such hydrogenations can be carried out e.g. at 20° to 200° C. at 1 to 200 bar, in the presence of conventional solvents such as methanol, tetrahydrofuran or dioxane, and preferably in the presence of bases. The bases can be present e.g. in equimolar or greater amounts, examples of possible bases being potassium carbonate or triethylamine. In such hydrogenations where $R^1$, $R^2$, $R^3$ and/or $R^4$=halogen, ring chlorine atoms can be hydrogenated at the same time.

The modification of 1,3-benzo- and 1,3-pyrido-dioxoles is illustrated by Examples 24 to 40.

It is extremely surprising that 1,2-dihydroxybenzenes and 2,3-dihydroxypyridines can be monoalkylated very selectively with hexafluorobut-2-enes by the processes according to the invention. A substantial degree of dialkylation and oligomerisation would have been expected to take place.

Fluorinated 1,3-benzo- and 1,3-pyrido-dioxoles of formula (I) can be used as intermediates for the preparation of biologically active compounds, for example plant protection agents.

For example, 1,3-benzo- and 1,3-pyrido-dioxoles of formula (I) which contain an amino group can be phosgenated, e.g. with phosgene or diphosgene, to convert the amino group to an isocyanato group, the resulting isocyanato-1,3-benzo- or -1,3-pyrido-dioxole can be reacted with a benzimidazole, e.g. of formula (VI):

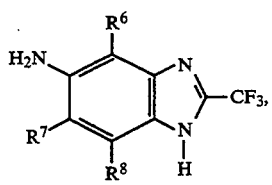

in which

R⁶, R⁷ and R⁸ independently of one another are each hydrogen, halogen, cyano or nitro, alkyl, alkoxy, alkylthio alkylsulphinyl, alkylsulphonyl or cycloalkyl, each of which is optionally substituted, fused dioxyalkylene which is optionally substituted, hydroxycarbonyl, alkylcarbonyl, alkoxycarbonyl or cycloalkoxycarbonyl, amino or aminocarbonyl, each of which is optionally substituted, or aryl, aryloxy, arylthio, arylsulphinyl, arylsulphonyl, arylsulphonyloxy, arylcarbonyl, aryloxycarbonyl, arylazo or arylthiomethylsulphonyl, each of which is optionally substituted, at least one of the substituents R⁶, R⁷ or R⁸ being halogenoalkyl except for the chloromethyl radical, halogenoalkoxy, halogenoalkylthio, halogenoalkylsulphinyl, halogenoalkylsulphonyl or alkylsulphonyl, fused dioxyalkylene which is optionally substituted, hydroxycarbonyl, alkylcarbonyl, alkoxycarbonyl or cycloalkoxycarbonyl, or aryl, arylthio, arylsulphinyl, arylsulphonyl, arylsulphonyloxy, arylcarbonyl, aryloxycarbonyl, arylazo or arylthiomethylsulphonyl, each of which is optionally substituted, (for preparation see e.g. J. Fluorine Chem. 56, 1 (1992) and references cited therein), to give a urea derivative, e.g. of formula (VII):

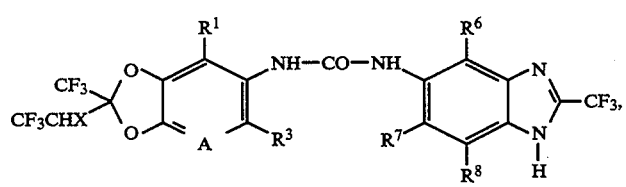

in which

R¹, R³, X and A are as defined for formula (I) and R⁶, R⁷ and R⁸ are as defined for formula (VI), and this can be alkylated with an alkylating agent, e.g. of formula (VIII):

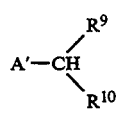

(VIII)

in which

A' is a suitable leaving group, e.g. halogen, especially chlorine, bromine or iodine, or alkylsulphonyloxy, alkoxysulphonyloxy or arylsulphonyloxy, each of which is optionally substituted, especially methanesulphonyloxy, trifluoromethanesulphonyloxy, methoxysulphonyloxy, ethoxysulphonyloxy or p-toluenesulphonyloxy, or an alcohol, alkanoyloxy, alkoxy or hydroxy group, especially an acetoxy or methoxy group, R⁹ is hydrogen, alkyl, alkoxy or optionally substituted aryl and R¹⁰ is hydroxy or cyano, or alkyl, alkenyl, alkinyl, alkoxy, alkenyloxy, alkinyloxy, alkylthio, amino, aminocarbonyl, alkylcarbonyl, alkoxycarbonyl, alkylcarbonyloxy, dialkoxyphosphonyl, (hetero)aryl, (hetero)arylcarbonyl, (hetero)aryloxycarbonyl, (hetero)arylcarbonyloxy or (hetero)arylaminocarbonylaminocarbonyloxy, each of which is optionally substituted, to give a urea derivative, e.g. of formula (VII), except that the nitrogen atom adjacent to R⁸ is substituted by a radical

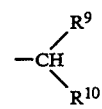

The reactions (phosgenation, urea formation from isocyanate and amine, alkylation) required for the preparation of such urea derivatives can be carried out in a manner known per se.

The majority of the compounds of formula (VIII) are known. Examples of those which are not known are compounds of formula (VIII'):

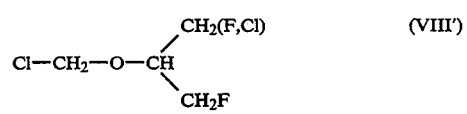

These can be obtained by reacting the corresponding isopropanol with formaldehyde and hydrogen chloride at −20° to +20° C. The compounds of formula (VIII') and their preparation form the subject of another patent application in the name of the same Applicant.

(VII)

A further possibility is for example to convert 1,3-benzo- and 1,3-pyrido-dioxoles of formula (I) which contain two adjacent amino groups, with trifluoroacetic acid, to the corresponding benzimidazole, e.g. of formula (IX):

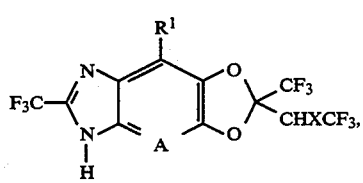

in which

A, R¹ and X are as defined for formula (I).

These can be alkylated, e.g. with compounds of formula (VIII), to give benzimidazole derivatives, e.g. of formula (IX), except that the nitrogen atom adjacent to A is substituted by a radical

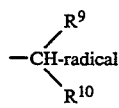

Compounds which contain

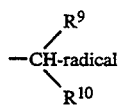

water. The product was extracted with diethyl ether and the organic phase was washed twice with 10% by Weight aqueous sodium hydroxide solution and once with water. After drying over magnesium sulphate, the solution was concentrated and subjected to fractional distillation under vacuum. The yield was 258 g (=84% of theory). The boiling point was 63° C. at 12 mbar. The NMR spectra showed the following characteristic absorptions: $^{19}$F NMR: −66.8 and −79.7 ppm. $^1$H NMR: 4.71 ppm.

EXAMPLES 3 to 10

The following Examples were carried out analogously to Examples 1 and 2 (see Table 1 for details):

TABLE 1

| Example no. | Analogous to Example no. | Dihydroxybenzene of formula (II) used, A = C—R$^4$, R$^4$ = H | | | Product of formula (I) obtained, A = C—R$^4$, R$^4$ = H, R$^1$ to R$^3$ as for dihydroxybenzene used | | | Characteristic absorptions in NMR spectra (ppm) | | |
|---|---|---|---|---|---|---|---|---|---|---|
| | | R$^1$ | R$^2$ | R$^3$ | X | Yield | B.p. (°C./mbar) | $^{19}$F | | $^1$H |
| 3 | 1 | Br | H | H | H | 19% | 37/10 | −61.1 | −86.8 | 3.04 |
| 4 | 1 | H | CHO | H | H | 33% | 75/0.04 | −59.0 | −84.6 | 3.08 |
| 5 | 2 | H | CHO | H | Cl | 51% | 81/0.06 | −68.6 | −81.4 | 4.87 |
| 6 | 2 | H | CN | H | Cl | 48% | 76/0.03 | −68.6 | −81.4 | 4.80 |
| 7 | 2 | NO$_2$ | H | H | Cl | 72% | n.d. | −68.6 | −81.1 | 4.89 |
| 8 | 2 | H | phenyl | H | Cl | 85% | n.d. | −68.6 | −81.5 | 4.70 |
| 9 | 2 | H | CH$_3$ | H | Cl | 70% | 95/16 | −68.6 | −81.6 | 4.69 |
| 10 | 2 | H | —CH=CH—CH=CH— | | Cl | 92% | crystalline | −68.7 | −81.3 | 4.75 | n.d. = not determined radicals but otherwise have formulae (VII) and (IX) are suitable for example for controlling animal jests such as arthropods and nematodes, especially insects and arachnids, which occur as pests in agriculture, in forests, in the protection of stored products and materials and in the hygiene sector. They are effective against species of normal sensitivity and resistance and against all or individual stages of development. These substances and their preparation form the subject of another patent application in the name of the same Applicant.

EXAMPLES

EXAMPLE 1

2-(2,2,2-Trifluoroethyl)-2-trifluoromethyl-1,3-benzodioxole 11 g of pyrocatechol were dissolved in 200 ml of dimethylformamide, and 18 g of 45% by weight aqueous sodium hydroxide solution were added. 20 g of 2-chloro-1,1,1,4,4,4-hexafluorobut-2-ene were added dropwise to the mixture at 75° C. The reaction mixture was subsequently stirred for 30 minutes at 75° C. and then poured into 500 ml of ice-water and extracted with diethyl ether. The organic phase was washed with water, dried over magnesium sulphate and concentrated. The product was finally distilled under high vacuum. The yield was 15 g (=56%) and the boiling point was 60° C. at 10 mbar. The NMR spectra showed the following characteristic absorptions: $^{19}$F NMR: −59.0 and −84.6 ppm. $^1$H NMR: 3.02 ppm.

EXAMPLE 2

2-(1-Chloro-2,2,2-trifluoroethyl)-2-trifluoromethyl-1,3-benzodioxole 110 g of pyrocatechol were dissolved in 1500 ml of acetonitrile, and 200 g of triethylamine were added. 235 g of 2,3-dichloro-1,1,1,4,4,4-hexafluorobut-2-ene were added dropwise to the mixture at 75° C. The reaction mixture was subsequently stirred for 2 hours at 75° C. 1200 ml of the solvent were then distilled off under vacuum and the residue was taken up in 1500 ml of

EXAMPLE 11

2-(1-Chloro-2,2,2-trifluoroethyl)-2-trifluoromethyl-[1,3]-dioxolo[4,5-b]pyridine 11 g of 2,3-dihydroxypyridine were reacted with 23.5 g of 2,3-dichloro-1,1,1,4,4,4-hexafluorobut-2-ene as described in Example 2. After distillation under high vacuum, the product was obtained in an amount of 15.5 g (=50% of theory) in the form of colourless crystals. The NMR spectra showed the following characteristic absorptions: $^{19}$F NMR: −68.5 and −81.6 ppm. $^1$H NMR: 4.81 ppm.

EXAMPLE 12

2-(1,1,1,4,4,4-Hexafluorobut-2-enoxy)-methoxybenzene 260 g of 2-methoxyphenol were dissolved in 1 l of dimethylformamide (technical grade), and 220 g of 45% sodium hydroxide solution were added. 400 g of 2-chloro-1,1,1,4,4,4-hexafluorobut-2-ene were then added dropwise at 22° C. with stirring The mixture was subsequently stirred for 2 hours at 22° C. 1.5 l of ice-water were then added and the mixture was extracted with methylene chloride The combined organic phases were washed twice with 10% sodium hydroxide solution and once with saturated NaCl solution, dried over MgSO$_4$ and distilled. The yield was 329 g (58% of theory) and the boiling point was 68°–70° C. at 12 mbar. The NMR spectra showed the following characteristic absorptions: $^{19}$F NMR: −57.6 and −67.9 ppm. $^1$H NMR: 5.92 ppm.

EXAMPLE 13

2-(1,1,1,4,4,4-Hexafluorobut-2-enoxy)-phenol 286.1 g of 2-(1,1,1,4,4,4-hexafluorobut-2-enoxy)-methoxybenzene from Example 12 were dissolved in a mixture of 500 ml of glacial acetic acid and 500 ml of 48% hydrobromic acid, and 5 g of triethylbenzylammonium chloride were added. The mixture was stirred at a bath temperature of 150° C. until monitoring by gas chromatography showed that conversion was complete. It was then left to cool and 2 kg of ice-water were added. The aqueous phase was extracted thoroughly with $CH_2Cl_2$. After drying over $MgSO_4$, the solvent was stripped off and the residue was distilled under vacuum. The yield was 200 g (50% of theory) and the boiling point was 80° C. at 16 mbar. The NMR spectra showed the following characteristic absorptions: $^{19}F$ NMR: $-59.6$ and $-69.6$ ppm. $^1H$ NMR: 6.1 ppm.

EXAMPLE 14

2-(2,2,2-Trifluoroethyl)-2-trifluoromethyl-1,3-benzodioxole 200 g of 2-(1,1,1,4,4,4-hexafluorobut-2-enoxy)-phenol from Example 13 were dissolved in 400 ml of acetonitrile, and 5 g of triethylamine were added. The mixture was stirred for 4 h at 70° C. It was then distilled under vacuum. The yield was 162 g (81% of theory) and the boiling point was 60° C. at 10 mbar. The NMR spectra showed the following characteristic absorptions: $^{19}F$ NMR: $-59.0$ and $-84.6$ ppm. $^1H$ NMR: 3.02 ppm.

EXAMPLE 15

2-(2-Chloro-1,1,1,4,4,4-hexafluorobut-2-enoxy)-1-benzyloxybenzene 20 g of 2-benzyloxyphenol were dissolved in 100 ml of dimethylformamide, and 9 g of 45% sodium hydroxide solution were added. 23 g of 2,3-dichloro-1,1,1,4,4,4-hexafluorobut-2-ene were then added dropwise at room temperature. When the exothermic reaction had subsided, the mixture was stirred for 1 hour at room temperature, added to water and extracted with tert-butyl methyl ether. After drying over $MgSO_4$, the solvent was stripped off. The yield was 29 g (74% of theory). The NMR spectrum showed the following characteristic absorptions: $^{19}F$ NMR: $-59.5$, $-60.5$, $-61.7$ and $-62.8$ ppm.

EXAMPLE 16

2-(2-Chloro-1,1,1,4,4,4-hexafluorobut-2-enoxy)-phenol 24.4 g of 2-(2-chloro-1,1,1,4,4,4-hexafluorobut-2-enoxy)-1-benzyloxybenzene from Example 15 were dissolved in 150 ml of tetrahydrofuran and treated with 3 bar of hydrogen at room temperature for 4 hours, in the presence of 2 g of Pd/C (10%). The mixture was then filtered and the filtrate was concentrated and distilled under vacuum. The yield was 13.2 g (69% of theory) and the boiling point was 56° C. at 0.15 mbar.

EXAMPLE 17

2-(1-Chloro-2,2,2-trifluoroethyl)-2-trifluoromethyl-1,3-benzodioxole 11.7 g of 2-(2-chloro-1,1,1,4,4,4-hexafluorobut-2-enoxy)phenol from Example 16 were dissolved in 40 ml of tertbutyl methyl ether, and 40 ml of 1 N sodium hydroxide solution were added. After stirring for 30 minutes at room temperature, the organic phase was separated off, dried over $MgSO_4$ and distilled. The yield was 10 g (88% of theory) and the boiling point was 63° C. at 12 mbar. The NMR spectra showed the following characteristic absorptions: $^{19}F$ NMR: $-66.8$ and $-79.7$ ppm. $^1H$ NMR: 4.71 ppm.

EXAMPLE 18

2,2-Dimethyl-4-(1,1,1,4,4,4-hexafluorobut-2-enoxy)-1,3-benzodioxole (formula V, $R^5$ together wit $R^1$=—C(CH$_3$)—O— radical)

46 g of 2,2-dimethyl-4-hydroxy-1,3-benzodioxole (formula IV, $R^5$ together with $R^3$=—C(CH$_3$)$_2$—O— radical) were dissolved in 200 ml of N-methylpyrrolidone, and 31 g of 40% by weight aqueous sodium hydroxide solution were added. 54.8 g of 2-chloro-1,1,1,4,4,4-hexafluorobut-2-ene were then added dropwise at room temperature, with stirring. After subsequent stirring for 1 hour, the reaction mixture was poured into water and extracted with tert-butyl methyl ether. The organic phase was washed with 10% by weight aqueous sodium hydroxide solution and dried over magnesium sulphate and the readily volatile components were removed on a rotary evaporator. The residue consisted of 73.8 g (=80% of theory) of a product with a purity of 95% according to gas chromatography. The characteristic absorptions in the NMR spectra were as follows: $^{19}F$ NMR: $-58.1$ and $-68.5$ ppm. $^1H$ NMR: 6.73, 6.55, 6.03 and 1.70 ppm.

EXAMPLE 19

1,2-Dihydroxy-3-(1,1,1,4,4,4-hexafluorobut-2-enoxy)-benzene 65 g of the product of Example 18 were boiled under reflux with 200 ml of concentrated aqueous hydrochloric acid for 4 hours, with stirring. The reaction mixture was then diluted with 300 ml of water and extracted with methylene chloride. After drying over magnesium sulphate, the solvent was stripped off from the organic phase to give 54 g of a 90% pure product. Recrystallisation from cyclohexane gave colourless crystals melting at 105° C. The characteristic absorptions in the NMR spectra were as follows: $^{19}F$ NMR: $-57.7$ and $-67.7$ ppm. $^1H$ NMR: 6.77, 6.50, 6.21 and 5.42 ppm.

EXAMPLE 20

2-(2,2,2-Trifluoroethyl)-2-(trifluoromethyl)-4-hydroxy-1,3-benzodioxole (formula (I), $R^1$=OH, X=H, A=CH, $R^2$ and $R^3$=H)

43.5 g of the product of Example 19 were dissolved in 300 ml of acetonitrile, and 1.5 g of triethylamine were added at room temperature. After stirring for 2 hours at room temperature, the solvent was stripped off and the residue was distilled under vacuum. The yield was 17 g (=39% of theory), the boiling point was 85° C. at 0.15 mbar and the melting point was 65° C. The characteristic absorptions in the NMR spectra were as follows: $^{19}F$ NMR: $-59.0$ and $-84.5$ ppm. $^1H$ NMR: 6.80, 6.55, 6.2 and 3.01 ppm.

EXAMPLE 21

2,2-Dimethyl-4-(3-chloro-1,1,1,4,4,4-hexafluorobut-2-enoxy)-1,3-benzodioxole (formula (V), $R^1$ and $R^5$ together=—C(CH$_3$)$_2$—O—, $X^1$=Cl, $R^2$+$R^3$=H, A=CH)

33.2 g of 2,2-dimethyl-4-hydroxy-1,3-benzodioxole were reacted with 47 g of 2,3-dichloro-1,1,1,4,4,4-hexafluorobut-2-ene analogously to Example 18. The product obtained was distilled under vacuum to give a 1:1 molar mixture of cis and trans isomers. The yield was 51 g (=70% of theory) and the boiling point was 70° C. at 0.15 mbar. The characteristic absorptions in the NMR spectra were as follows: $^{19}F$ NMR: $-60.0$, $-61.6$, $-62.2$ and $-63.4$ ppm. $^1H$ NMR: 6.79, 6.65 to 6.48 and 1.7 ppm.

EXAMPLE 22

1,2-Dihydroxy-3-(3-chloro-1,1,1,4,4,4-hexafluorobut-2-enoxy)-benzene (formula (V), $R^1$=OH, $R^2$+$R^3$=H, A=CH, $R^5$=H, $X^1$=Cl)

18 g of the product of Example 21 were reacted with 50 ml of concentrated hydrochloric acid analogously to Example 19 to give 15.7 g of a 97% pure product. The product was a 1:1 molar mixture of the cis and trans isomers. The characteristic absorptions in the NMR spectra were as follows: $^{19}F$ NMR: $-60.2$, $-61.3$, $-62.2$ and $-63.3$ ppm. $^{1}H$ NMR: 6.80, 6.45 and 6.25 ppm.

EXAMPLE 23

2-(1-Chloro-2,2,2-trifluoroethyl)-2-trifluoromethyl-4-hydroxy-1,3-benzodioxole 15 g of the product of Example 22 were dissolved in 50 ml of acetonitrile, and 1 ml of triethylamine was added. After stirring for 15 minutes, the solvent was stripped off and the residue was distilled under vacuum. The product was purified by being taken up in diethyl ether and filtered over silicon dioxide. The diethyl ether was stripped off to leave 10.5 g of product (=70% of theory). The melting point was 139° to 141° C. The characteristic absorptions in the NMR spectra were as follows: $^{19}F$ NMR: $-66.6$ and $-79.3$ ppm. $^{1}H$ NMR: 8.4, 6.76, 6.60, 6.50 and 4.70 ppm.

EXAMPLE 24

5-Bromo-2-(2,2,2-trifluoroethyl)-2-trifluoromethyl-1,3-benzodioxole 54.4 g of 2-(2,2,2-trifluoroethyl)-2-trifluoromethyl-1,3-benzodioxole were dissolved in 300 ml of carbon tetrachloride, and 0.4 g of anhydrous iron(III) chloride was added. 32 g of bromine were then added dropwise at the reflux temperature and the mixture was subsequently stirred until conversion was complete (monitoring by gas chromatography). The reaction mixture was then left to cool, washed with 10% by weight aqueous sodium hydrogen-sulphite solution and water, dried over magnesium sulphate and concentrated. The residue was distilled under vacuum. The yield was 58 g (83% of theory) and the boiling point was 80° C. at 14 mbar. The characteristic absorptions in the NMR spectra were as follows: $^{19}F$ NMR: $-59.2$ and $-84.9$ ppm. $^{1}H$ NMR: 3.02 ppm.

EXAMPLE 25

5-Bromo-2-(1-chloro-2,2,2-trifluoroethyl)-2-trifluoromethyl-1,3-benzodioxole 51 g of 2-(1-chloro-2,2,2-trifluoroethyl)-2-trifluoromethyl-1,3-benzodioxole from Example 2 or 17 were dissolved in 300 ml of carbon tetrachloride, and 0.5 g of anhydrous $FeCl_3$ was added. 32 g of bromine were then added and the mixture was stirred for 3 hours under reflux. After cooling, it was washed with 10% $NaHSO_3$ solution, dried over $MgSO_4$ and distilled. The yield was 49 g (63% of theory) and the boiling point was 94°–98° C. at 8 mbar.

EXAMPLE 26

5-Chloro-6-formyl-2-(1-chloro-2,2,2-trifluoroethyl)-2-trifluoromethyl-1,3-benzodioxole 67 g of the aldehyde of Example 5 were dissolved in 150 ml of chloroform. Chlorine gas was passed in at 50°–60° C. until the reaction was complete. The crude yield after the solvent had been stripped off was 73 g (98% of theory). The NMR spectra showed the following characteristic absorptions: $^{19}F$ NMR: $-68.6$ and $-81.4$ ppm. $^{1}H$ NMR: 4.81 ppm.

EXAMPLE 27

5-Nitro-2-(2,2,2-trifluoroethyl)-2-trifluoromethyl-1,3-benzodioxole

A solution of 54.4 g of 2-(2,2,2-trifluoroethyl)-2-trifluoromethyl-1,3-benzodioxole in 75 ml of methylene chloride was added dropwise at 10° C. to a mixture of 40 ml of 65% by weight nitric acid and 40 ml of concentrated sulphuric acid. The reaction mixture was subsequently stirred for 1 hour at room temperature and then poured into ice-water, the organic phase was separated off and the aqueous phase was extracted with methylene chloride. The combined organic phases were washed with water and dried and the readily volatile components were removed. The residue consisted of 95 g of product (=86% of theory) melting at 87° to 88° C. The NMR spectra showed the following characteristic absorptions: $^{19}F$ NMR: $-59.0$ and $-69.4$ ppm. $^{1}H$ NMR: 3.10 ppm.

EXAMPLE 28

5-Nitro-2-(1-chloro-2,2,2-trifluoroethyl)-2-trifluoromethyl-1,3-benzodioxole 613 g of 2-(1-chloro-2,2,2-trifluoroethyl)-2-trifluoromethyl-1,3-benzodloxole from Example 2 were dissolved in 1.2 l of methylene chloride and added dropwise at 0°–10° C. to a mixture of 400 ml of 65% nitric acid and 400 ml of conc. sulphuric acid. The reaction mixture was subsequently stirred for 2 hours at room temperature. It was then added cautiously to 2 l of ice-water and extracted with methylene chloride. The combined organic phases were washed twice with water, dried and concentrated. The yield was 652 g (93% of theory). The NMR spectra showed the following characteristic absorptions: $^{19}F$ NMR: $-66.4$ and $-79.2$ ppm. $^{1}H$ NMR: 4.81 ppm.

EXAMPLE 29

5,6-Dinitro-2-(2,2,2-trifluoroethyl)-2-trifluoromethyl-1,3-benzodioxole 317 g of the product of Example 27 were taken and a mixture of 250 ml of 100% by weight nitric acid and 350 ml of concentrated sulphuric acid was added dropwise, with stirring. The reaction mixture was stirred for 2 hours at 55° C. It was then left to cool and poured into ice-water. The product was extracted with methylene chloride, the extract was washed with sodium hydrogen-carbonate solution until the washings were neutral, and dried, and the readily volatile components were removed on a rotary evaporator. The yield was 339 g (=94% of theory) and the melting point was 101° to 103° C. The NMR spectra showed the following characteristic absorptions: $^{19}F$ NMR: $-60.9$ and $-86.5$ ppm. $^{1}H$ NMR: 3.18 ppm.

EXAMPLE 30

5,6-Dinitro-2-(1-chloro-2,2,2-trifluoroethyl)-2-trifluoromethyl-1,3-benzodioxole 352 g of 5-nitro-2-(1-chloro-2,2,2-trifluoroethyl)-2-trifluoromethyl-1,3-benzodioxole from Example 28 were taken and a mixture of 250 ml of 100% by weight nitric acid and 350 ml of concentrated sulphuric acid was added. The reaction mixture was stirred for 2 hours at 60° C. After cooling, it was poured into ice-water and extracted with methylene chloride. After washing with sodium hydrogencarbonate solution and drying, the extract was concentrated on a rotary evaporator. The yield was 392 g (91% of theory) and the melting point was 125° C. The NMR spectra showed the following characteristic absorptions: $^{19}$F NMR: −68.5 and −81.0 ppm. $^1$H NMR: 4.86 ppm.

EXAMPLE 31

5-Chlorosulphonyl-2-(2,2,2-trifluoroethyl)-2-trifluoromethyl-1,3-benzodioxole 136 g of 2-(2,2,2-trifluoroethyl)-2-trifluoromethyl-1,3-benzodioxole were dissolved in 125 ml of chloroform. 175 g of chlorosulphonic acid were added dropwise at 0° C., with stirring, and the reaction mixture was subsequently stirred at room temperature until the evolution of gas had ended. It was then poured into 750 g of ice-water, the phases were separated and the aqueous phase was extracted with chloroform. The combined organic phases were washed with ice-water and sodium hydrogencarbonate solution and dried over magnesium sulphate and the readily volatile components were removed on a rotary evaporator to give 133 g of product (=72% of theory). The melting point was 55° to 57° C. $^{19}$F NMR: −60.8 and −86.5 ppm. $^1$H NMR: 3.13 ppm.

EXAMPLE 32

5-Cyano-2-(2,2,2-trifluoroethyl)-2-trifluoromethyl-1,3-benzodioxole 35 g of the product of Example 24 were dissolved in 75 ml of dimethylformamide, and 10.5 g of copper(I) cyanide were added. The mixture was stirred for 8 hours at 160° C. The hot mixture was then discharged into 100 ml of ice-water, and 30 g of 1,2-diaminoethane were added. After stirring for 30 minutes, the organic phase was separated off and the aqueous phase was extracted with methylene chloride. The combined organic phases were washed with a solution of 30 g of 1,2-diaminoethane in 75 ml of water, dried over magnesium sulphate and distilled under high vacuum to give 20.5 g of product (=69% of theory). The boiling point was 110° C. at 0.02 mbar. =$^{19}$F NMR: −58.1 and −84.6 ppm. $^1$H NMR: 3.08 ppm.

EXAMPLE 33

5-Amino-2-(2,2,2-trifluoroethyl)-2-trifluoromethyl-1,3-benzodioxole 57.4 g of the product of Example 27 were dissolved in 400 ml of tetrahydrofuran and hydrogenated with hydrogen at 50 bar for 5 hours at 30° C. in the presence of 4 g of catalyst (palladium-on-charcoal, 10% by weight). After filtration, the solvent was removed and the residue was distilled under high vacuum to give 37 g of product (=63% of theory) with a boiling point of 83° C. at 0.07 mbar. $^{19}$F NMR: −59.0 and −84.6 ppm. $^1$H NMR: 2.98 ppm.

EXAMPLE 34

4-Amino-2-(1-chloro-2,2,2-trifluoroethyl)-2-trifluoromethyl-1,3-benzodioxole 84 g of 4-nitro-2-(1-chloro-2,2,2-trifluoroethyl)-2-trifluoromethyl-1,3-benzodioxole from Example 7 were dissolved in 500 ml of tetrahydrofuran and hydrogenated with 15-20 bar of hydrogen for 5 hours at room temperature on 5 g of palladium-on-charcoal (5%). The mixture was then filtered and the filtrate was concentrated and distilled under vacuum. The yield was 31 g (40% of theory) and the boiling point was 70° C. at 0.1 mbar. The NMR spectra showed the following characteristic absorptions: $^{19}$F NMR: −68.6 and −81.5 ppm. $^1$H NMR: 4.69 ppm.

EXAMPLE 35

5-Amino-2-(1-chloro-2,2,2-trifluoroethyl)-2-trifluoromethyl-1,3-benzodioxole 72 g of 5-nitro-2-(1-chloro-2,2,2-trifluoroethyl)-2-trifluoromethyl-1,3-benzodioxole from Example 28 were dissolved in 500 ml of tetrahydrofuran and hydrogenated with 15-20 bar of hydrogen for 5 hours at room temperature on 5 g of palladium-on-charcoal (5%). The mixture was then filtered and the solvent was stripped off under vacuum. The yield was 60 g (93% of theory) and the boiling point was 80°-82° C. at 0.1 mbar. The NMR spectra showed the following characteristic absorptions: $^{19}$F NMR: −66.5 and −79.4 ppm. $^1$H NMR: 4.68 ppm.

EXAMPLE 36

5-Isocyanato-2-(2,2,2-trifluoroethyl)-2-trifluoromethyl-1,3-benzodioxole 37 g of the product of Example 33 were dissolved in 50 ml of absolute 1,4-dioxane, and a solution of 13.5 g of diphosgene in 80 ml of absolute 1,4-dioxane was added. The mixture was then stirred for 6 hours at 110° C. (bath temperature), the solvent was then removed under vacuum and the remaining residue was subjected to fractional distillation under vacuum to give 18 g of product (=44% of theory) with a boiling point of 63° C. at 0.1 mbar. NMR: −59.3 and −85.0 ppm. $^1$H NMR: 3.0 ppm.

EXAMPLE 37

5,6-Diamino-2-(2,2,2-trifluoroethyl)-2-trifluoromethyl-1,3-benzodioxole 39 g of the product of Example 29 were dissolved in 2000 ml of tetrahydrofuran, and 20 g of catalyst (palladium-on-charcoal, 5% by weight) were added. The reaction mixture was hydrogenated with hydrogen at 25 to 30 bar for 13 hours at room temperature. It was then filtered and the solvent was stripped off under vacuum to leave a solid. The yield was 274 g (=96% of theory). $^{19}$F NMR: −61.2 and −86.6 ppm. $^1$H NMR: 3.02 ppm.

EXAMPLE 38

2-(1-Chloro-2,2,2-trifluoroethyl)-2-(trifluoromethyl)-5-hydroxy-1,3-benzodioxole 50 g of 2(1-chloro-2,2,2-trifluoroethyl)-2-(trifluoromethyl)-5-formyl-1,3-benzodioxole were dissolved in 500 ml of methylene chloride, and 53 g of 70% by weight m-chloroperbenzoic acid were added. The reaction mixture was stirred under reflux for 6 hours. It was then cooled and the precipitate formed was filtered off. The filtrate was washed with 5% by weight aqueous sodium hydrogen-sulphite solution and saturated aqueous sodium hydrogen-carbonate solution and concentrated on a rotary evaporator. The remaining residue was dissolved in 300 ml of diethyl ether, and 100 ml of 1 N sodium hydroxide solution were added at room temperature. When the reaction was complete, the phases were separated and the organic phase was washed with saturated aqueous ammonium chloride solution, dried over magnesium sulphate and subjected to fractional distillation under vacuum. The yield was 26 g (=54% of theory) and the boiling point was 95° C. at 0.07 mbar. $^{19}$F NMR: −68.6 and −81.6 ppm. $^1$H NMR: 4.70 ppm.

EXAMPLE 39

4-Bromomethyl-2-(1-chloro-2,2,2-trifluoroethyl)-2-trifluoromethyl-1,3-benzodioxole 64 g of 4-methyl-2-(1-chloro-2,2,2-trifluoroethyl)-2-trifluoromethyl-1,3-benzodioxole from Example 9 were dissolved in 500 ml of carbon tetrachloride, and 36 g of N-bromosuccinimide and 0.5 g of AIBN (azoisobutyronitrile) were added. The mixture was stirred under reflux for 3 hours and then cooled and filtered. The solvent was stripped off and the residue was distilled under vacuum. The yield was 57 g (71% of theory) and the boiling point was 80°–82° C. at 0.1 mbar. The NMR spectrum showed the following characteristic absorption: $^1$H NMR: 4.72 ppm.

EXAMPLE 40

2-(2,2,2-Trifluoroethyl)-2-trifluoromethyl-1,3-benzodioxole 306.5 g of 2-(1-chloro-2,2,2-trifluoroethyl)-2-trifluoromethyl-1,3-benzodioxole from Example 2 were dissolved in 500 ml of THF, and 101 g of triethylamine and 30 g of palladium-on-charcoal (5% by weight) were added. The mixture was then hydrogenated with 100 bar of hydrogen for 48 h at 110° C. It was then filtered, the solvent was stripped off and the residue was fractionated under vacuum. The yield was 126 g (46% of theory) and the boiling point was 60° C. at 10 mbar. The NMR spectra showed the following characteristic absorptions: $^{19}$F NMR: −59.0 and −84.6 ppm. $^1$H NMR: 3.02 ppm.

What is claimed is:

1. A fluorinated 1,3-benzo-dioxole of the formula (I)

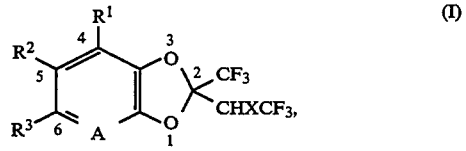

in which

A represents C-R$^4$

X represents hydrogen, fluorine, chlorine or bromine and

R$^1$ to R$^4$ can be identical or different from one another and each represent hydrogen, halogen, C$_1$-C$_6$-alkyl, C$_1$-C$_6$-alkoxy, halogeno-C$_1$-C$_6$-alkyl, C$_6$-C$_{10}$-aryl, CHO, COOH, COCl, CN, OH, NCO, COO—C$_1$-C$_6$-alkyl, NO$_2$, NH$_2$, NH—C$_1$-C$_6$-alkyl, N(C$_1$-C$_6$-alkyl)$_2$, SO$_2$Cl, SO$_3$H, SO$_3$Na or SO$_3$K, at least one of R$^2$ and R$^3$ represents an NH$_2$ radical.

2. A fluorinated 1,3-benzo-dioxole of claim 1, in which in: formula (I), the remaining radical or radicals, provided they are not hydrogen, independently of one another represent chlorine, bromine, methyl, ethyl, CH$_2$Cl, CH$_2$Br, phenyl, CHO, COOH, OH, NCO, NO$_2$, NH$_2$ and/or SO$_2$Cl.

* * * * *

UNITED STATES PATENT AND TRADEMARK OFFICE
CERTIFICATE OF CORRECTION

PATENT NO. : 5,420,309

DATED : May 30, 1995

INVENTOR(S) : Bohm, et al

It is certified that error appears in the above-indentified patent and that said Letters Patent is hereby corrected as shown below:

Column 16, claim 1, line 2, delete ":" and after " (I)," insert —at least two radicals $R^1$ to $R^4$ represent hydrogen and —.

Signed and Sealed this

Twenty-ninth Day of August, 1995

Attest:

BRUCE LEHMAN

*Attesting Officer*     *Commissioner of Patents and Trademarks*